US010485870B2

(12) United States Patent
Zhang et al.

(10) Patent No.: US 10,485,870 B2
(45) Date of Patent: Nov. 26, 2019

(54) STABLE PHARMACEUTICAL SOLUTION FORMULATION OF GLP-1R ANTIBODY FUSION PROTEIN

(71) Applicant: Gmax Biopharm LLC., Hangzhou (CN)

(72) Inventors: Cheng Zhang, Hangzhou (CN); Hua Zhang, Hangzhou (CN); Kesuo Fan, Hangzhou (CN); Yong Guo, Hangzhou (CN); Shuqian Jing, Hangzhou (CN)

(73) Assignee: Gmax Biopharm LLC., Hangzhou (CN)

( * ) Notice: Subject to any disclaimer, the term of this patent is extended or adjusted under 35 U.S.C. 154(b) by 103 days.

(21) Appl. No.: 15/547,727

(22) PCT Filed: Feb. 3, 2016

(86) PCT No.: PCT/CN2016/073279
§ 371 (c)(1),
(2) Date: Jul. 31, 2017

(87) PCT Pub. No.: WO2016/127887
PCT Pub. Date: Aug. 18, 2016

(65) Prior Publication Data
US 2018/0000934 A1    Jan. 4, 2018

(30) Foreign Application Priority Data

Feb. 11, 2015    (CN) .......................... 2015 1 0071304

(51) Int. Cl.
| A61K 39/395 | (2006.01) |
| A61K 9/08 | (2006.01) |
| A61K 47/12 | (2006.01) |
| C07K 16/28 | (2006.01) |
| A61K 38/26 | (2006.01) |
| A61K 47/18 | (2017.01) |
| A61K 47/26 | (2006.01) |
| C07K 14/605 | (2006.01) |

(52) U.S. Cl.
CPC .......... *A61K 39/39591* (2013.01); *A61K 9/08* (2013.01); *A61K 38/26* (2013.01); *A61K 39/3955* (2013.01); *A61K 47/12* (2013.01); *A61K 47/183* (2013.01); *A61K 47/26* (2013.01); *C07K 14/605* (2013.01); *C07K 16/2869* (2013.01)

(58) Field of Classification Search
CPC ................ A61K 39/39591; A61K 9/08; C07K 16/2869; C07K 14/72
See application file for complete search history.

(56) References Cited

U.S. PATENT DOCUMENTS

| 5,899,883 | A | 5/1999 | Chern et al. |
| 6,006,753 | A | 12/1999 | Efendic |
| 6,191,102 | B1 | 2/2001 | DiMarchi et al. |
| 6,277,819 | B1 | 8/2001 | Efendic |
| 6,348,447 | B1 | 2/2002 | Hellstrom et al. |
| 6,989,148 | B2 | 1/2006 | Dupre |
| 7,998,929 | B2 | 8/2011 | Sato |
| 2003/0224983 | A1 | 12/2003 | Nielsen |
| 2006/0275288 | A1 | 12/2006 | Grihalde et al. |
| 2009/0098130 | A1 | 4/2009 | Bradshaw et al. |
| 2009/0181037 | A1 | 7/2009 | Heavner |
| 2009/0021453 | A1 | 8/2009 | Holmes et al. |
| 2009/0214534 | A1 | 8/2009 | Holmes et al. |
| 2010/0196405 | A1 | 8/2010 | Ng |
| 2011/0020345 | A1 | 1/2011 | Herring et al. |
| 2011/0098443 | A1 | 4/2011 | Karyn et al. |
| 2012/0270782 | A1 | 10/2012 | Gopinath et al. |
| 2016/0362498 | A1 | 12/2016 | Zhang et al. |

FOREIGN PATENT DOCUMENTS

| CN | 102961745 A | 3/2013 |
| EP | 2238985 A1 | 10/2010 |
| WO | 2000/016797 A2 | 3/2000 |
| WO | 2002/046227 A2 | 6/2002 |
| WO | 2006/059106 A2 | 6/2006 |
| WO | 2006/068910 A1 | 6/2006 |
| WO | 2007/039140 A1 | 4/2007 |
| WO | 2009/009562 A2 | 1/2009 |

OTHER PUBLICATIONS

Bonner-Weir, "Life and death of the pancreatic beta cells," Trends Endocrinol Metab., 2000, 11, 375-378.
Defronzo, "Lilly lecture 1987. The triumvirate: beta-cell, muscle, liver. A collusion responsible for NIDDM," Diabetes, 1988, 37, 667-687.
Doyle et al., "Mechanisms of action of glucagon-like peptide 1 in the pancreas," Pharmacol. Ther. 2007, 113, 546-593.

(Continued)

*Primary Examiner* — Ruixiang Li
(74) *Attorney, Agent, or Firm* — Jones Day

(57) ABSTRACT

Disclosed is a stable pharmaceutical solution formulation of a GLP-1R antibody fusion protein, comprising a therapeutically effective amount of the GLP-1R antibody fusion protein, an amino acid, a surfactant and a buffer system. The final concentration of the amino acid is 1-500 mM, the final concentration of the surfactant is 0.01%-0.5%, and the pH value of the stable solution formulation is from 5.0 to 8.0. The stable solution formulation of the present invention can be used in the treatment of diabetes, obesity and conditions associated therewith.

21 Claims, No Drawings
Specification includes a Sequence Listing.

(56) References Cited

OTHER PUBLICATIONS

Drucker et al., "Glucagon-like peptide I stimulates insulin gene expression and increases cyclic AMP levels in a rat islet cell line," Proc. Natl. Acad. Sci. USA, 1987, 84, 3434-3438.

Hui et al., "Glucagon-like peptide-1 inhibits apoptosis of insulin-secreting cells via a cyclic 5'-adenosine monophosphate-dependent protein kinase A- and a phosphatidylinositol 3-kinase-dependent pathway," Endocrinology, 2003, 144, 1444-1455.

Kahn and Goldfine, "Molecular determinants of insulin action," J. Diabetes Complications, 1993, 7, 92-105.

Kahn et al., "Obesity, body fat distribution, insulin sensitivity and Islet beta-cell function as explanations for metabolic diversity," J. Nutr., 2001, 131, 354S-360S.

Lam et al., "Free fatty acid-induced hepatic insulin resistance: a potent role for protein kinase C-delta," Am. J. Physiol. Endocrinol. Metab., 2002, 283, E682-E691.

Lin et al., "Molecular modeling of the three-dimensional structure of GLP-1R and its interactions with several agonists," J. Mol. Model., 2009, 15, 53-65.

Lund et al., "Glucagon-like peptide-1 receptor agonists for the treatment of type 2 diabetes: differences and similarities," Eur. J. Intern. Med. 2014, 25, 407-414.

Nauck et al., "Glucagon-like peptide 1 (GLP-1) as a new therapeutic approach for type 2-diabetes," Exp. Clin. Endocrinol. Diabetes., 1997, 105, 187-195.

Orskov et al., "Tissue and plasma concentrations of amidated and glycine-extended glucagon-like peptide I in humans," Diabetes, 1994, 43, 535-539.

Perfetti et al., "Glucagon-like peptide-1 induces cell proliferation and pancreatic-duodenum homeobox-1 expression and increases endocrine cell mass in the pancreas of old, glucose-intolerant rats," Endocrinology (2000) 141:4600-4605.

Samson et al., "GLP-1R agonist therapy for diabetes: benefits and potential risks," Curr. Opin. Endocrinol. Diabetes Obes., 2013, 20, 87-97.

Todd et al., "Glucagon-like peptide-1 (GLP-1): a trial of treatment in non-insulin-dependent diabetes mellitus," Eur. J. Clin. Invest., 1997, 27, 533-536.

Unger et al., "Role of glucagon in diabetes," Arch. Intern. Med., 1977, 137, 482-491.

Verspohl, "Novel pharmacological approaches to the treatment of type 2 diabetes," Pharmacol. Rev. 2012; 64, 188-237.

Wettergren et al., "Truncated GLP-1 (proglucagon 78-107-amide) inhibits gastric and pancreatic functions in man," Dig. Dis. Sci., 1993, 38, 665-673.

Weyer et al., "The natural history of insulin secretory dysfunction and insulin resistance in the pathogenesis of type 2 diabetes mellitus," J. Clin. Invest., 1999, 104, 787-794.

SEQUENCE LISTING

<160> NUMBER OF SEQ ID NOS: 12

<210> SEQ ID NO 1
<211> LENGTH: 157
<212> TYPE: PRT
<213> ORGANISM: Artificial Sequence
<220> FEATURE:
<223> OTHER INFORMATION: Synthetic construct

<400> SEQUENCE: 1

```
His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
            20                  25                  30

Ser Gly Gly Gly Ser Gly Gly Gly Ser Gly Gly Gly Ser Asp Ile Val
        35                  40                  45

Met Thr Gln Thr Pro Leu Ser Leu Ser Val Thr Pro Gly Gln Pro Ala
    50                  55                  60

Ser Ile Ser Cys Lys Ser Thr Lys Ser Leu Leu Asn Ser Asp Gly Phe
65                  70                  75                  80

Thr Tyr Leu Asp Trp Tyr Leu Gln Lys Pro Gly Gln Pro Pro Gln Leu
                85                  90                  95

Leu Ile Tyr Leu Val Ser Asn Arg Phe Ser Gly Val Pro Asp Arg Phe
            100                 105                 110

Ser Gly Ser Gly Ser Gly Thr Asp Phe Thr Leu Lys Ile Ser Arg Val
        115                 120                 125

Glu Ala Glu Asp Val Gly Val Tyr Tyr Cys Phe Gln Ser Asn Tyr Leu
    130                 135                 140

Pro Phe Thr Phe Gly Gln Gly Thr Lys Val Glu Ile Lys
145                 150                 155
```

<210> SEQ ID NO 2
<211> LENGTH: 164
<212> TYPE: PRT
<213> ORGANISM: Artificial Sequence
<220> FEATURE:
<223> OTHER INFORMATION: Synthetic construct

<400> SEQUENCE: 2

```
His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Ser Ala Thr Gly Gly Ser Gly Ser Gly Ala Ser Ser Gly Ser Gly Ser
        35                  40                  45

Ala Thr Gly Ser Asp Ile Val Met Thr Gln Thr Pro Leu Ser Leu Ser
    50                  55                  60

Val Thr Pro Gly Gln Pro Ala Ser Ile Ser Cys Lys Ser Thr Lys Ser
65                  70                  75                  80

Leu Leu Asn Ser Asp Gly Phe Thr Tyr Leu Asp Trp Tyr Leu Gln Lys
                85                  90                  95
```

```
Pro Gly Gln Pro Pro Gln Leu Leu Ile Tyr Leu Val Ser Asn Arg Phe
            100                 105                 110

Ser Gly Val Pro Asp Arg Phe Ser Gly Ser Gly Ser Gly Thr Asp Phe
            115                 120                 125

Thr Leu Lys Ile Ser Arg Val Glu Ala Glu Asp Val Gly Val Tyr Tyr
            130                 135                 140

Cys Phe Gln Ser Asn Tyr Leu Pro Phe Thr Phe Gly Gln Gly Thr Lys
145                 150                 155                 160

Val Glu Ile Lys

<210> SEQ ID NO 3
<211> LENGTH: 153
<212> TYPE: PRT
<213> ORGANISM: Artificial Sequence
<220> FEATURE:
<223> OTHER INFORMATION: Synthetic construct

<400> SEQUENCE: 3

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
            20                  25                  30

Ser Gly Gly Gly Ser Gly Gly Ser Gly Gly Ser Ala Ile Gln
            35                  40                  45

Met Thr Gln Ser Pro Ser Ser Val Ser Ala Ser Ile Gly Asp Arg Val
            50                  55                  60

Thr Ile Thr Cys Arg Ala Ser Gln Asn Ile Asn Leu Leu Ala Trp
65                  70                  75                  80

Tyr Gln Gln Lys Pro Gly Lys Ala Pro Lys Leu Leu Ile Tyr Thr Ala
            85                  90                  95

Ser Ser Leu Gln Ser Glu Val Pro Ser Arg Phe Ser Gly Ser Gly Ser
            100                 105                 110

Gly Thr Asp Phe Thr Leu Thr Ile Ser Ser Leu Gln Pro Glu Asp Phe
            115                 120                 125

Ala Ile Tyr Cys Cys Gln Gln Ala His Arg Phe Pro Pro Thr Phe Gly
            130                 135                 140

Gln Gly Thr Lys Val Glu Ile Arg Arg
145                 150

<210> SEQ ID NO 4
<211> LENGTH: 160
<212> TYPE: PRT
<213> ORGANISM: Artificial Sequence
<220> FEATURE:
<223> OTHER INFORMATION: Synthetic construct

<400> SEQUENCE: 4

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Ser Ala Thr Gly Gly Ser Gly Ser Thr Ala Ser Ser Gly Ser Gly Ser
            35                  40                  45

Ala Thr Gly Ser Ala Ile Gln Met Thr Gln Ser Pro Ser Ser Val Ser
            50                  55                  60

Ala Ser Ile Gly Asp Arg Val Thr Ile Thr Cys Arg Ala Ser Gln Asn
65                  70                  75                  80
```

-continued

Ile Asn Asn Leu Leu Ala Trp Tyr Gln Gln Lys Pro Gly Lys Ala Pro
                85                  90                  95

Lys Leu Leu Ile Tyr Thr Ala Ser Ser Leu Gln Ser Glu Val Pro Ser
            100                 105                 110

Arg Phe Ser Gly Ser Gly Ser Gly Thr Asp Phe Thr Leu Thr Ile Ser
        115                 120                 125

Ser Leu Gln Pro Glu Asp Phe Ala Ile Tyr Cys Cys Gln Gln Ala His
    130                 135                 140

Arg Phe Pro Pro Thr Phe Gly Gln Gly Thr Lys Val Glu Ile Arg Arg
145                 150                 155                 160

<210> SEQ ID NO 5
<211> LENGTH: 151
<212> TYPE: PRT
<213> ORGANISM: Artificial Sequence
<220> FEATURE:
<223> OTHER INFORMATION: Synthetic construct

<400> SEQUENCE: 5

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
            20                  25                  30

Ser Gly Gly Gly Ser Gly Gly Ser Gly Gly Ser Glu Ile Val
        35                  40                  45

Leu Thr Gln Ser Pro Gly Thr Leu Ser Leu Ser Pro Gly Glu Arg Ala
    50                  55                  60

Thr Leu Ser Cys Arg Ala Ser Ser Val Thr Tyr Ile His Trp Tyr
65              70                  75                  80

Gln Gln Lys Pro Gly Gln Ala Pro Arg Leu Leu Ile Tyr Gly Thr Ser
                85                  90                  95

Asn Leu Ala Ser Gly Ile Pro Asp Arg Phe Ser Gly Ser Gly Ser Gly
            100                 105                 110

Thr Asp Phe Thr Leu Thr Ile Ser Arg Leu Glu Pro Glu Asp Phe Ala
        115                 120                 125

Val Tyr Tyr Cys Gln Gln Trp Ser Ser Asn Pro Pro Thr Phe Gly Gln
    130                 135                 140

Gly Thr Lys Leu Glu Ile Lys
145                 150

<210> SEQ ID NO 6
<211> LENGTH: 158
<212> TYPE: PRT
<213> ORGANISM: Artificial Sequence
<220> FEATURE:
<223> OTHER INFORMATION: Synthetic construct

<400> SEQUENCE: 6

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Ser Ala Thr Gly Gly Ser Gly Ser Ala Ser Ser Gly Ser
        35                  40                  45

Ala Thr Gly Ser Glu Ile Val Leu Thr Gln Ser Pro Gly Thr Leu Ser
    50                  55                  60

Leu Ser Pro Gly Glu Arg Ala Thr Leu Ser Cys Arg Ala Ser Ser Ser

```
                65                  70                  75                  80
Val Thr Tyr Ile His Trp Tyr Gln Gln Lys Pro Gly Gln Ala Pro Arg
                    85                  90                  95

Leu Leu Ile Tyr Gly Thr Ser Asn Leu Ala Ser Gly Ile Pro Asp Arg
                100                 105                 110

Phe Ser Gly Ser Gly Ser Gly Thr Asp Phe Thr Leu Thr Ile Ser Arg
            115                 120                 125

Leu Glu Pro Glu Asp Phe Ala Val Tyr Tyr Cys Gln Gln Trp Ser Ser
        130                 135                 140

Asn Pro Pro Thr Phe Gly Gln Gly Thr Lys Leu Glu Ile Lys
145                 150                 155
```

<210> SEQ ID NO 7
<211> LENGTH: 120
<212> TYPE: PRT
<213> ORGANISM: Artificial Sequence
<220> FEATURE:
<223> OTHER INFORMATION: Synthetic construct

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Gly Met Ala Trp Val Arg Gln Ala Pro Gly Lys Gly Leu Glu Trp Val
        35                  40                  45

Ser Phe Ile Ser Asn Leu Ser Tyr Arg Ile Tyr Tyr Ala Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Met Ala Pro Asn Trp Tyr Phe Asp Val Trp Gly Gln
            100                 105                 110

Gly Thr Thr Val Thr Val Ser Ser
        115                 120
```

<210> SEQ ID NO 8
<211> LENGTH: 125
<212> TYPE: PRT
<213> ORGANISM: Artificial Sequence
<220> FEATURE:
<223> OTHER INFORMATION: Synthetic construct

<400> SEQUENCE: 8

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Gly Gly Gly Ser Gly Ser Tyr Arg Tyr Tyr Tyr Gly Leu
            100                 105                 110

Asp Val Trp Gly Gln Gly Thr Thr Val Thr Val Ser Ser
        115                 120                 125

<210> SEQ ID NO 9
<211> LENGTH: 114
<212> TYPE: PRT
<213> ORGANISM: Artificial Sequence
<220> FEATURE:
<223> OTHER INFORMATION: Synthetic construct

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Lys Gly Leu Glu Trp Ile
        35                  40                  45

Gly Met Ile Trp Gly Gly Gly Ser Thr Asp Tyr Asn Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Leu Pro Gly Asp Tyr Trp Gly Gln Gly Thr Leu Val Thr Val
            100                 105                 110

Ser Ser

<210> SEQ ID NO 10
<211> LENGTH: 106
<212> TYPE: PRT
<213> ORGANISM: Homo sapiens

<400> SEQUENCE: 10

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 11
<211> LENGTH: 101
<212> TYPE: PRT
<213> ORGANISM: Homo sapiens

<400> SEQUENCE: 11

Ala Pro Ser Val Thr Leu Phe Pro Pro Ser Ser Glu Glu Leu Gln Ala
1               5                   10                  15

```
Asn Lys Ala Thr Leu Val Cys Leu Ile Ser Asp Phe Tyr Pro Gly Ala
                20                  25                  30

Val Thr Val Ala Trp Lys Ala Asp Ser Ser Pro Val Lys Ala Gly Val
            35                  40                  45

Glu Thr Thr Thr Pro Ser Lys Gln Ser Asn Asn Lys Tyr Ala Ala Ser
        50                  55                  60

Ser Tyr Leu Ser Leu Thr Pro Glu Gln Trp Lys Ser His Arg Ser Tyr
65                  70                  75                  80

Ser Cys Gln Val Thr His Glu Gly Ser Thr Val Glu Lys Thr Val Ala
                85                  90                  95

Pro Thr Glu Cys Ser
            100

<210> SEQ ID NO 12
<211> LENGTH: 326
<212> TYPE: PRT
<213> ORGANISM: Homo sapiens

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

```
Leu Thr Val Asp Lys Ser Arg Trp Gln Gln Gly Asn Val Phe Ser Cys
    290             295                 300

Ser Val Met His Glu Ala Leu His Asn His Tyr Thr Gln Lys Ser Leu
305             310                 315                 320

Ser Leu Ser Pro Gly Lys
                325
```

STABLE PHARMACEUTICAL SOLUTION FORMULATION OF GLP-1R ANTIBODY FUSION PROTEIN

CROSS REFERENCE TO RELATED APPLICATIONS

This application is a National Stage of International Application No. PCT/CN2016/073279, filed Feb. 3, 2016, which claims the benefit of the priority of Chinese Patent Application No. 201510071304.1, filed Feb. 11, 2015; the disclosure of each of which is incorporated herein by reference in its entirety.

REFERENCE TO A SEQUENCE LISTING

The present specification is being filed with a Sequence Listing in Computer Readable Form (CRF), which is entitled 14254-005-999_SEQLIST.txt of 17,105 bytes in size and was created Jul. 17, 2017; the content of which is incorporated herein by reference in its entirety.

FIELD

The present invention relates to the technical field of biomedicines, especially relating to a stable pharmaceutical solution formulation of a GLP-1R antibody fusion protein.

BACKGROUND

GLP-1 derivatives are used in clinical trials to treat type II diabetes and obesity (Gallwitz B, *Eur. Endocrinol.*, 2015; 11:21-5). GLP-1 induces multiple biological effects, for example, stimulation of insulin secretion, inhibition of glucagon secretion, inhibition of gastric emptying, inhibition of gastric and intestinal movement, as well as induction of loss of body weight (Lund A et al., *Eur. J. Intern. Med.*, 2014; 25:407-14). One prominent characteristic of GLP-1 is its capability of stimulating the secretion of insulin without the risk of inducing hypoglycemia, which is one of the concern in insulin treatment and some other oral therapies that promote endogenous insulin secretion. Endogenous GLP-1 is degraded very quickly and its extremely short half-life limits the effectiveness of GLP-1 as a therapeutic peptide.

Currently, there are various ways to prolong the half-live of GLP-1 and its derivatives and maintain their biological activity at the same time (Verspohl E J, *Pharmacol. Rev,* 2012; 64:A-AX), including fusion of GLP-1 and its derivatives with an IgG Fc fragment or human serum albumin (HSA). The new method we have chosen is fusing GLP-1 with a full-length anti-GLP-1R antibody (IgG). The IgG can extend the in vivo half-life of its fusion partner and its own half-life in human is 21 days. In addition to maintaining the biological activity of GLP-1, a GLP-1R antibody fusion protein has advantageous stability provided by the IgG moiety. At the same time, the IgG moiety provides the GLP-1R antibody fusion protein molecular targeting properties, thus increasing the possibility of the interactions between GLP-1 and GLP-1R. Furthermore, the antibody molecule has lower immunogenicity than most of other commonly used fusion partners. As to a drug for a long-term or even life-long use, low immunogenicity is a necessity.

Fusion proteins are often produced by mammalian cell lines, for example, CHO, SP2/0 or NSO. It is noted in the present invention that, when CHO cells were used to produce a GLP-1R antibody fusion protein, the fusion protein was subjected to degradation by endogenous proteases or under certain cell culturing physicochemical conditions. The degradation process was faster and more apparent under low pH conditions, and on top of that, the GLP-1R antibody fusion protein was more prone to aggregation when pH was higher than 7. Furthermore, it was discovered in the present invention that under refrigeration conditions (2-8° C.) and in a single buffer solution (for example, a citrate buffer system), the solubility of the GLP-1R antibody fusion protein is too low to meet the requirements for therapeutic dosages. In the present invention, the problems mentioned above are solved through pH control, using a specific combination of certain excipients and a specific concentration of the GLP-1R antibody fusion protein.

SUMMARY

The objective of the present invention is to provide a stable pharmaceutical solution formulation of a GLP-1R antibody fusion protein, and the formulation is stable with a long half-life in vivo and efficacious, and can be used for the treatment of diabetes, obesity and related diseases.

To solve the technical problems mentioned above, the present invention provides the following technical solutions.

A stable pharmaceutical solution formulation of a GLP-1R antibody fusion protein, comprises a therapeutically effective amount of the GLP-1R antibody fusion protein, an amino acid, a surfactant and a buffer system, wherein the final concentration of the amino acid is 1-500 mM, the final concentration of the surfactant is 0.01%-0.5%, and the pH of the stable solution formulation is from 5.0 to 8.0.

To overcome the problems that a solution formulation of the GLP-1R antibody fusion protein is unstable at low pH and easily aggregated at high pH, and the GLP-1R antibody fusion protein does not have an sufficient solubility in a single buffer solution, the present invention provides a physiochemically stable formulation comprising a GLP-1R antibody fusion protein, and further comprising a buffering system, an amino acid as a stabilizer and an osmoregulator, and a surfactant. The stable solution formulation is stable for at least 6 months at 25° C. Preferably, the stable solution formulation of the present invention comprises the GLP-1R antibody fusion protein at the final concentration of about 0.1-100 mg/mL, a citrate buffer at the concentration of 5-30 mM, TWEEN-80 at the final concentration of 0.01%-0.2%, and L-arginine at the final concentration of 80-200 mM, wherein the pH is from 5 to 8. The stable solution formulation enhances the solubility of the GLP-1R antibody fusion protein and its stability under special circumstances, especially at high temperatures. The present invention also includes a method of treating diabetes, obesity and related diseases, which comprises administering the GLP-1R antibody fusion protein formulation of the present invention.

Preferably, the final concentration of the amino acid is 80-200 mM, the final concentration of the surfactant is 0.01%-0.2%, and the buffer system is a citrate buffer, and the pH of the stable solution formulation is from 5.5 to 7.0.

Preferably, the concentration of the citrate buffer is 5-30 mM.

Preferably, the amino acid is L-arginine, the final concentration of L-arginine is 100-180 mM, the surfactant is TWEEN-80, and the final concentration of TWEEN-80 is 0.05%-0.15%.

Preferably, the final concentration of the therapeutically effective amount of the GLP-1R antibody fusion protein is 0.1 mg/mL-100 mg/mL.

Preferably, the final concentration of the therapeutically effective amount of GLP-1R antibody fusion protein is 5 mg/mL-40 mg/mL.

Preferably, the amino acid sequence of the light chain variable domain of the GLP-1R antibody fusion protein is one selected from SEQ ID NO: 1, SEQ ID NO: 2, SEQ ID NO: 3, SEQ ID NO: 4, SEQ ID NO: 5, SEQ ID NO: 6, and the amino acid sequence of the heavy chain variable domain is one selected from SEQ ID NO: 7, SEQ ID NO: 8, SEQ ID NO: 9.

Preferably, the amino acid sequence of the light chain constant domain of the GLP-1R antibody fusion protein is SEQ ID NO: 10 or SEQ ID NO: 11, and the amino acid sequence of the heavy chain constant domain is SEQ ID NO: 12.

The GLP-1R antibody fusion protein of the present invention comprises GLP-1 or an analog thereof, which is fused at its C-terminus to the N-terminus of the light chain of a GLP-1R antibody by a peptide linker. The antibody fusion protein has a similar or improved biological activity and an extended half-life compared to GLP-1 and its analogs. The sequence of the light chain variable domain of the preferred GLP-1R antibody fusion protein comprises all or part of SEQ ID NO: 1, 2, 3, 4, 5 or 6, the sequence of the light chain constant domain comprises all or part of SEQ ID NO: 10 or 11, the sequence of the heavy chain variable domain comprises all or part of SEQ ID NO: 7, 8 or 9, and the sequence of the heavy chain constant domain comprises all or part of SEQ ID NO: 12. The sequence of the light chain variable domain of the more preferred GLP-1R antibody fusion protein is substantially SEQ ID NO: 1, 2, 3, 4, 5 or 6, the sequence of the light chain constant domain is substantially SEQ ID NO: 10 or 11, the sequence of the heavy chain variable domain is substantially SEQ ID NO: 7, 8 or 9, and the sequence of the heavy chain constant domain is substantially SEQ ID NO: 12. The sequence of the light chain variable domain of the most preferred GLP-1R antibody fusion protein is SEQ ID NO: 1, 2, 3, 4, 5 or 6, the sequence of the light chain constant domain is SEQ ID NO: 10 or 11, the sequence of heavy chain variable domain is SEQ ID NO: 7, 8 or 9, and the sequence of the heavy chain constant domain is SEQ ID NO: 12.

The stable solution formulation of the present invention can be used to treat diabetes or obesity.

The stable solution formulation of the present invention can be used to treat irritable bowel syndrome, and other diseases that benefit from decreasing plasma glucose, inhibition of gastric and/or bowel movement, inhibition of gastric and/or intestinal emptying, or inhibition of food intake.

The beneficial effects of the present invention are: stability, an in vivo long half-life, good efficacy, and suitability for the treatment of diabetes, obesity, irritable bowel syndrome and related diseases.

DETAILED DESCRIPTION

Through the following specific embodiments, the technical solutions of the present invention are further illustrated.

In this invention, unless referred specifically, the raw materials and instruments and the like employed are all commercially available or are commonly used in the art. The methods of the following embodiments, if not indicated specifically, are all conventional methods in the art.

The preparation of the GLP-1R antibody fusion protein of the present invention is described in a prior patent applicant: CN104371019A, WO 2015/021871.

Biological activity refers to the ability of a GLP-1R antibody fusion protein to bind and activate GLP-1R in vivo to elicit a response. Responses include, but are not limited to, promotion of insulin secretion, inhibition of glucagon secretion, inhibition of appetite, induction of weight loss, induction of satiety, inhibition of pancreatic β-cell apoptosis and induction of pancreatic β-cell proliferation.

The stable pharmaceutical solution formulation of a GLP-1R antibody fusion protein comprises the GLP-1R antibody fusion protein in a buffer, which further comprises an amino acid as a stabilizer and an osmoregulator, and a surfactant. At 25° C., the stable solution formulation is stable for at least 6 months, and at 25° C., more precisely, the stable solution formulation is stable for 6 months to 8 months, 6 months to 12 months, 6 months to 18 months, 6 months to 24 months, 8 months to 12 months, 8 months to 18 months, 8 months to 24 months, 12 months to 18 months, 12 months to 24 months, 18 months to 24 months.

The buffer system used in the present invention includes, but is not limited to. one or several of the following organic or inorganic compounds: citric acid, salts of citric acid, ascorbic acid, salts of ascorbic acid, gluconic acid, salts of gluconic acid, carbonic acid, salts of carbonic acid, tartaric acid, salts of tartaric acid, succinic acid, salts of succinic acid, acetic acid, salts of acetic acid, phthalic acid, salts of phthalic acid, phosphoric acid, phosphate, hydrochloric acid, Tris, thomethamine, and an amino acid, including, but not limited to, histidine, arginine, glycine.

The osmoregulator as defined in the present invention is a substance capable of increasing the osmotic pressure of a formulation upon addition. The osmoregulatory of the present invention are free amino acids, including, but not limited to, arginine, histidine, methionine, lysine, ornithine, leucine, isoleucine, alanine, glycine, glutamic acid and aspartic acid. The basic amino acid is preferably arginine, histidine, lysine or a combination thereof. The amino acid can be added in the form of a salt of an amino acid where the added amino acid can be a D-amino acid such as D-arginine or an L-amino acid such as L-arginine.

Within the scope of the present invention, the added amino acid is not limited to functioning just as an osmoregulator, but also as a stabilizer at the same time, including, but not limited to, arginine, histidine, methionine, lysine, ornithine, leucine, isoleucine, alanine, glycine, glutamine, glutamic acid, asparagine, aspartic acid, phenylalanine, tyrosine, serine, proline and tryptophan. Preferably, the concentration of the amino acid as a stabilizer and osmoregulator in the present invention is from 1 to 500 mM.

Surfactants as defined in the present invention are amphiphilic organic compounds, that is, compounds contain groups having different soluble properties. Typically, these compounds contain both lipophilic hydrocarbon groups and hydrophilic ionic groups. The surfactants of the present invention include, but are not limited to, sorbitan fatty acid esters, e.g., sorbitan monocaprylate, sorbitan monolaurate, sorbitan monopalmitate, sorbitan trioleate; glycerine fatty acid esters, e.g., glycerine monocaprylate, glycerine monomyristate, glycerine monostearate; polyglycerine fatty acid esters, e.g., decaglyceryl monostearate, decaglyceryl di stearate, decaglyceryl monolinoleate; polyoxyethylene sorbitan fatty acid esters, e.g., polyoxyethylene sorbitan monolaurate, wherein polyoxyethylene (20) sorbitan monolaurate is TWEEN-20 and polyoxyethylene sorbitan monopalmitate is TWEEN-40, polyoxyethylene sorbitan monooleate, wherein polyoxyethylene (80) sorbitan monooleate is TWEEN-80, polyoxyethylene sorbitan monostearate, wherein polyoxyethylene (60) sorbitan monostearate is TWEEN-60, polyoxyethylene sorbitan trioleate is TWEEN-85, and polyoxyethylene sorbitan tristearate is TWEEN-65; polyoxyethylene sorbitol fatty acid esters, e.g., polyoxyethylene sorbitol tetrastearate, polyoxyethylene sorbitol tetraoleate; polyoxyethylene glycerine fatty acid esters, e.g., polyoxyethylene glyceryl monostearate; polyethylene glycol fatty acid esters, e.g., polyethylene glycol distearate; polyoxyethylene alkyl ethers, e.g., polyoxyethylene lauryl ether; polyoxyethylene polyoxypropylene alkyl ethers, e.g., polyoxyethylene polyoxypropylene glycol, polyoxyethylene polyoxypropylene propyl ether, polyoxyethylene polyoxypropylene cetyl ether; polyoxyethylene alkylphenyl ethers, e.g., polyoxyethylene nonylphenyl ether; polyoxyethylene hydrogenated castor oils, e.g., polyoxyethylene castor oil, polyoxyethylene hydrogenated castor oil; polyoxyethylene beeswax derivatives, e.g., polyoxyethylene sorbitol beeswax; polyoxyethylene lanolin derivatives, e.g., polyoxyethylene lanolin; and polyoxyethylene fatty acid amides, e.g., polyoxyethylene stearic acid amide; C10-C18 alkyl sulfates, e.g., sodium cetyl sulfate, sodium lauryl sulfate, sodium oleyl sulfate; polyoxyethylene C10-C16 alkyl ether sulfate with an average of 2 to 4 moles of ethylene oxide units added, e.g., sodium polyoxyethylene lauryl sulfate; and C1-C18 alkyl sulfosuccinate ester salts, e.g., sodium lauryl sulfosuccinate ester; and natural surfactants such as lecithin, glycerophospholipid, sphingophospholipids, e.g., sphingomyelin, and sucrose esters of C12-C18 fatty acids. The surfactant used in the present invention can include one or more of the surfactants described hereinabove. More suitable surfactants are polyoxyethylene sorbitan fatty acid esters, e.g., TWEEN-20, TWEEN-40, TWEEN-60 and TWEEN-80.

The stable pharmaceutically solution formulation of a GLP-1R fusion protein comprises the GLP-1R antibody fusion protein at a final concentration from about 0.1 to about 100 mg/mL. The preferred concentration (mg/mL) of the GLP-1R antibody fusion protein ranges from about 0.1 to 1, 1 to 5, 5 to 10, 5 to 20, 10 to 20, 20 to 30, 20 to 40, 30 to 40, 40 to 50, 50 to 60, 60 to 70, 70 to 80, 80 to 90, 90 to 100 mg/mL. More preferably, the concentration (mg/mL) of the GLP-1R antibody fusion protein is about 0.1, about 0.25, about 0.5, about 1, about 2, about 3, about 4, about 5, about 6.5, about 8, about 10, about 12.5, about 15, about 17.5, about 20, about 22.5, about 25, about 27.5, about 30, about 32.5, about 35, about 37.5, about 40, about 45, about 50, about 55, about 60, about 65, about 70, about 75, about 80, about 85, about 90, about 95, about 100 mg/mL.

The preferred buffer system of the stable solution formulation is a citrate salt at it's a concentration ranging from about 5 to 30 mM. More preferably, the citrate concentration (mM) is ranging from about 5 to 25, 5 to 20, 5 to 15, 5 to 12.5, 5 to 10, 7.5 to 30, 7.5 to 25, 7.5 to 20, 7.5 to 15, 7.5 To 12.5, 7.5 to 10, 8 to 30, 8 to 25, 8 to 20, 8 to 15, 8 to 12.5, 8 to 11, 8 to 10, 9 to 30, 9 to 25, 9 to 20, 9 to 15, 9 to 12.5, 10 to 30, 10 to 25, 10 to 20, 10 to 17.5, 10 to 15, 10 to 12.5, 12.5 to 30, 12.5 to 25, 12.5 to 20, 12.5 to 15, 15 to 30, 15 to 25, 15 to 20, 17.5 to 30, 17.5 to 25, 17.5 to 22.5, 17.5 to 20, 20 to 30, 20 to 27.5, 20 to 25, 20 to 22.5, 22.5 to 30, 22.5 to 27.5, 22.5 to 25, 25 to 30, 25 to 27.5, 27.5 to 30. A further preferred citrate concentration is about 5 to 20 mM. A particularly preferred citrate concentration is about 10, 10.0, 20 or 20.0 mM.

The pH of the stable pharmaceutical solution formulation of the GLP-1R fusion protein of the present invention ranges from about 5 to 8. The pH range provides acceptable stability for the formulation to maintain the solubility of the GLP-1R antibody fusion protein and to promote the activity of stimulating insulin secretion, and suitable for parenteral administration. The pH can be adjusted to the desired pH by adding an acid, e.g., HCl, or by adding a base, e.g., NaOH or by a combination of a citrate buffer and citric acid to achieve the desired buffer concentration and pH value. The preferred pH ranges from 5 to 7.75, 5 to 7.5, 5 to 7.25, 5 to 7.0, 5 to 6.75, 5 to 6.5, 5 to 6.25, 5 to 6.0, 5 to 5.75, 5 to 5.5, 5 to 5.25, 5.25 to 8.0, 5.25 to 7.75, 5.25 to 7.5, 5.25 to 7.25, 5.25 to 7.0, 5.25 to 6.75, 5.25 to 6.5, 5.25 to 6.25, 5.25 to 6.0, 5.25 to 5.75, 5.25 to 5.5, 5.5 to 8.0, 5.5 to 7.75, 5.5 to 7.5, 5.5 to 7.25, 5.5 to 7.0, 5.5 to 6.75, 5.5 to 6.5, 5.5 to 6.25, 5.5 to 6.0, 5.5 to 5.75, 5.75 to 8.0, 5.75 to 7.75, 5.75 to 7.5, 5.75 to 7.25, 5.75 to 7.0, 5.75 to 6.75, 5.75 to 6.5, 5.75 to 6.25, 5.75 to 6.0, 6.0 to 8.0, 6.0 to 7.75, 6.0 to 7.5, 6.0 to 7.25, 6.0 to 7.0, 6.0 to 6.75, 6.0 to 6.5, 6.0 to 6.25, 6.25 to 8.0, 6.25 to 7.75, 6.25 to 7.5, 6.25 to 7.25, 6.25 to 7.0, 6.25 to 6.75, 6.25 to 6.5, 6.5 to 8.0, 6.5 to 7.75, 6.5 to 7.5, 6.5 to 7.25, 6.5 to 7.0, 6.5 to 6.75, 6.75 to 8.0, 6.75 to 7.75, 6.75 to 7.5, 6.75 to 7.25, 6.75 to 7.0, 7.0 to 8.0, 7.0 to 7.75, 7.0 to 7.5, 7.0 to 7.25, 7.25 to 8.0, 7.25 to 7.5, 7.5 to 8.0, 7.5 to 7.75, 7.75 to 8.0. The further preferred pH ranges from 6 to 7, and particularly preferred pH is about 6.5 or 6.50.

The present invention preferably utilizes L-arginine as an osmoregulator and stabilizer for the stable pharmaceutical solution formulation of the GLP-1R fusion protein at a concentration ranging from 1 to 500 mM to stabilize the GLP-1R antibody fusion protein and to increase the solubility, and to adjust the osmotic pressure of the formulation so that it is suitable for parenteral administration and the like. The preferred L-arginine concentration ranges from 80 to 200 mM. Further preferred concentration ranges from 80 to 190, 80 to 180, 80 to 170, 80 to 160, 80 to 150, 80 to 140, 80 to 130, 80 to 120, 80 to 110, 80 to 100, 80 to 90, 90 to 200, 90 to 190, 90 to 180, 90 to 170, 90 to 160, 90 to 150, 90 to 140, 90 to 130, 90 to 120, 90 to 110, 90 to 100, 100 to 200, 100 to 190, 100 to 180, 100 to 170, 100 to 160, 100 to 150, 100 to 140, 100 to 130, 100 to 120, 100 to 110, 110 to 200, 110 to 190, 110 to 180, 110 to 170, 110 to 160, 110 to 150, 110 to 140, 110 to 130, 110 to 120, 120 to 200, 120 to 190, 120 to 180, 120 to 170, 120 to 160, 120 to 150, 120 to 140, 120 to 130, 130 to 200, 130 to 190, 130 to 180, 130 to 170, 130 to 160, 130 to 150, 130 to 140, 140 to 200, 140 to 190, 140 to 180, 140 to 170, 140 to 160, 140 to 150, 150 to 200, 150 to 190, 150 to 180, 150 to 170, 150 to 160, 160 to 200, 160 to 190, 160 to 180, 160 to 170, 170 to 200, 170 to 190, 170 to 180, 180 to 190, 190 to 200. Further preferred L-arginine concentration is 100 to 180 mM. Particularly preferred concentration is about 138 mM or about 138.0 mM.

The present invention preferably utilizes TWEEN-80 as a surfactant for the stable pharmaceutical solution formulation of a GLP-1R fusion protein at a concentration ranging from 0.01% to 0.5%. The preferred concentration of TWEEN-80 ranges from about 0.01% to about 0.2%, and the preferred concentration range is determined by the combination of GLP-1R antibody fusion protein and arginine so that the formation of soluble aggregates and insoluble particles are minimized. The further preferred concentration of TWEEN-80 ranges from about 0.01% to 0.2%, 0.01% to 0.15%, 0.01% to 0.1%, 0.01% to 0.05%, 0.01% to 0.025%, 0.025% to 0.2%, 0.025% to 0.15%, 0.025% to 0.1%, 0.025% to 0.05%, 0.05 to 0.2%, 0.05 to 0.15%, 0.05 to 0.1%, 0.05 to 0.075%, 0.075% to 0.2%, 0.075% to 0.15%, 0.075% to 0.1%, 0.1% to 0.2%, 0.1% to 0.15%, 0.15% to 0.2%. The further preferred TWEEN-80 concentration ranges from about 0.05% to about 0.15%. Particularly preferred TWEEN-80 concentration is about 0.1%.

A particularly preferred stable pharmaceutical solution formulation of a GLP-1R fusion protein comprises a GLP-1R antibody fusion protein at the concentration ranging from about 5 to about 20 mg/mL, a citrate buffer at the concentration of about 20 mM, TWEEN-80 at the concentration of about 0.1%, L-arginine at the concentration of about 138 mM, with a pH of about 6.5. Another particularly preferred stable pharmaceutical solution formulation of the GLP-1R fusion protein comprises a GLP-1R antibody fusion protein at the concentration ranging from about 20 to about 40 mg/mL, a citrate buffer at the concentration of about 20 mM, TWEEN-80 at the concentration of about 0.1%, L-arginine at the concentration of about 138 mM, with a pH of about 6.5. Another particularly preferred stable solution formulation comprises a GLP-1R antibody fusion protein at the concentration ranging from about 5 to about 20 mg/mL, a citrate buffer at the concentration ranging from about 5 to 20 mM, TWEEN-80 at the concentration ranging from about 0.05 to about 0.15%, L-arginine at the concentration ranging from about 100 to 180 mM, with a pH ranging from about 6.0 to 7. Another particularly preferred stable solution formulation comprises a GLP-1R antibody fusion protein at the concentration ranging from about 20 to about 40 mg/mL, a citrate buffer at the concentration ranging from about 5 to 20 mM, TWEEN-80 at the concentration ranging from about 0.05 to 0.15%, L-arginine at the concentration ranging from about 100 to 180 mM, with a pH ranging from about 6.0 to 7.

The administration of the stable solution formulation can be carried out by any effective route known to physicians skilled in the art. Parenteral administration is one of the methods. Parenteral administration is generally understood in the medical literature to inject a dosage form into an individual via a sterile syringe or some other mechanical devices such as an infusion pump. Parenteral routes can include intravenous, intramuscular, subcutaneous and intraperitoneal routes. Subcutaneous administration is the preferred route.

The stable solution formulation of the present invention can be used to treat an individual with non-insulin dependent diabetes mellitus or in progression to non-insulin dependent diabetes mellitus, insulin-dependent diabetes mellitus or obesity. The effective amount of the GLP-1R antibody fusion protein in the stable solution formulation described herein is an amount that causes the desired therapeutic and/or prophylactic effect when administered to an individual in need of GLP-1R stimulation without causing undesirable side effects.

It is preferable that the fusion proteins are administered either once every two weeks or once a week. Depending on the disease being treated, it may be necessary to administer the fusion protein more frequently such as two to three times per week.

The present invention will now be described by the following non-limiting examples.

SPECIFIC EMBODIMENTS OF THE INVENTION

A reporter gene assay was used to determine the in vitro activation of GLP-1R by a GLP-1 fusion protein.

The CHO-DHFR-cells co-expressing hGLP1R-CRE-luciferase were seeded into a 96-well cell culture plate with 20000 cells per well, and the plate was cultured at 37° C. overnight. The culture supernatant was removed the next day. The cells were washed twice with serum free medium and the residual liquid was removed by suction. After adding 100 μL of a GLP-1R antibody fusion protein sample that was pre-diluted with a serum free medium or a control, the cells were incubated at 37° C. for 4 h. After the incubation, 100 μL of BRIGHT-GLO™ chemiluminescence substrate (Promega) were added. Finally, the cell lysates were transferred into a white 96-well plate, and the relative luminescence intensities were recorded in a SPECTRAMAX® L (Molecular Devices) microplate reader. The dose-response curves (response intensities versus logarithmic concentrations) were analyzed using GraphPad to determine EC50. SEC-HPLC was used to analyze the purity of a GLP-1R antibody fusion protein.

Size-exclusion chromatography (SEC-HPLC) was used to determine the formation of aggregates (soluble aggregates) of a GLP-1R antibody fusion protein and the loss of its monomeric form. In AGILENT 1100 HPLC at 25° C., a TSK-G3000SWx1 high performance SEC column was flushed with 200 mM phosphate buffer (pH 6.8) as a mobile phase till the baseline of the UV absorbance was constant and stable. A stable pharmaceutical solution formulation of a GLP-1R antibody fusion protein at the concentration of 1-3 mg/mL (pre-diluted with the mobile phase) was injected in the amount of 50 μL. The sample was eluted with the mobile phase at a flow rate of 0.5 mL/min and the absorbance at UV 280 nm was recorded. After each run, the AUCs of absorbance peaks of the monomer (the main peak), dimers and multimers were calculated, the percentage of the AUC for the main peak versus the total AUC was calculated and reported as the purity of the sample.

EXAMPLE 1

Effect of pH on the Stability of a GLP-1R Antibody Fusion Protein pH can affect the solubility and stability of a GLP-1R antibody fusion protein, and is one of the most critical parameters in formulation. We determined the effect of pH on the stability of the GLP-1R antibody fusion protein in Example 1 by measuring the amount of soluble aggregates (dimers and multimers) formed, by measuring the ratio of the soluble aggregates formed (aggregate %) in each sample after 1 week or 3 weeks at 45° C. to determine the effect of each specific pH on the stability of the GLP-1R antibody fusion protein.

Stable pharmaceutical solution formulations of the GLP-1R fusion protein were prepared according to Table 1:

TABLE 1

GLP-1R antibody fusion protein formulation at different pH conditions

| GLP-1R antibody fusion protein 4.5 mg/mL | pH | Buffer |
|---|---|---|
| 1 | 6.5 | 0.1M PBS |
| 2 | 7 | 0.1M PBS |
| 3 | 7.5 | 0.1M PBS |
| 4 | 8 | 0.1M PBS |

A pharmaceutical stable solution formulation of a GLP-1R fusion protein was sterilized by filtration through 0.22 μm polyvinylidene difluoride (PVDF) membrane. The solution was stored at 45° C. in 2 mL borosilicate glass vials until analysis or up to 3 weeks. The ratio of soluble aggregates in each sample was determined by SEC-HPLC. As shown in Table 2, the ratio of soluble aggregates formed was the lowest at the particularly preferred pH of 6.5 and the stability of the formulation was the best; and the stability tends to increase as the pH decreases.

TABLE 2

Ratios of soluble aggregates formed in a GLP-1R antibody fusion protein formulation at different pH conditions

| GLP-1R antibody fusion protein 4.5 mg/mL | PH | Unit | Time point (week) 1 | 3 |
|---|---|---|---|---|
| 1 | 6.5 | % | 0.52 | 4.51 |
| 2 | 7.0 | % | 0.65 | 4.80 |
| 3 | 7.5 | % | 1.12 | 8.16 |
| 4 | 8.0 | % | 1.39 | 14.79 |

EXAMPLE 2

The Robustness of the Preferred Formulation

We conducted a robustness study on GLP-1R antibody fusion protein formulations at a concentration of 10 mg/mL to examine if errors (±15%) in the three most important excipients or factors (L-arginine, pH and TWEEN-80) which would have a significant effect on the quality and stability of the drug in the actual production process. Based on general formulation rules and the properties of the GLP-1R antibody fusion protein, the changes in the monomeric purity (that is, the percentage of the main peak) were chosen as the criteria.

Formulations of a GLP-1R antibody fusion protein were prepared according to Table 3 for DOE experiments:

TABLE 3

GLP-1R antibody fusion protein formulations for DOE experiments

| Formulation | L-arginine (mM) | TWEEN-80 (%) | pH |
|---|---|---|---|
| DOE-1 | 110 | 0.05 | 7 |
| DOE-2 | 110 | 0.15 | 6 |
| DOE-3 | 166 | 0.05 | 6 |
| DOE-4 | 166 | 0.15 | 7 |
| Preferred formulation (repeat 1) | 138 | 0.1 | 6.5 |
| Preferred formulation (repeat 2) | 138 | 0.1 | 6.5 |
| DOE-5 | 110 | 0.15 | 7 |
| DOE-6 | 110 | 0.05 | 6 |
| DOE-7 | 166 | 0.15 | 6 |
| DOE-8 | 166 | 0.05 | 7 |

Formulations were prepared and sterilized by filtration through 0.22 μm polyvinylidene difluoride (PVDF) membrane. The formulations were stored in a 2 mL glass vial at 40° C. until analysis or up to 1 month. The purity of each formulation was determined by SEC-HPLC. As shown in Table 4, in the range of pH 6 to 7, L-arginine 110 to 166 mM and TWEEN-80 concentration of 0.05% to 0.15%, the purity for each formulation appeared to be similar and there was no significant difference, indicating that the preferred formulation was of good robustness, the deviation in production should not significantly affect the stability of the actual formulation.

TABLE 4

Purities of GLP-1R antibody fusion protein formulations in DOE experiments

| Formulation | Purity (%) 0 Day | Purity (%) 15 Days | Purity (%) 1 Month |
|---|---|---|---|
| DOE-1 | 99.76 | 96.18 | 95.94 |
| DOE-2 | 99.77 | 95.59 | 95.34 |
| DOE-3 | 99.75 | 96.42 | 96.20 |
| DOE-4 | 99.75 | 94.43 | 94.10 |
| Preferred formulation (repeat 1) | 99.75 | 95.35 | 94.58 |
| Preferred formulation (repeat 2) | 99.75 | 95.84 | 94.88 |
| DOE-5 | 99.74 | 96.38 | 95.91 |
| DOE-6 | 99.74 | 95.60 | 95.23 |
| DOE-7 | 99.75 | 96.44 | 96.33 |
| DOE-8 | 99.75 | 94.43 | 93.77 |

EXAMPLE 3

Effect of the Concentrations of a GLP-1R Antibody Fusion Protein on the Formulation Stability We compared the performance of the preferred formulation at two different concentrations of the GLP-1R antibody fusion protein to determine whether the preferred formulation could provide acceptable stability at higher concentrations of GLP-1R antibody fusion protein to facilitate the high dosage use of GLP-1R antibody fusion protein in practice. We selected 10 and 20 mg/mL of the GLP-1R antibody fusion protein for comparison.

Formulations of the GLP-1R antibody fusion protein were prepared according to Table 5:

TABLE 5

Formulations of the GLP-1R antibody fusion protein at different protein concentrations

| No. | GLP-1R antibody fusion protein concentration (mg/mL) | Citrate concentration (mM) | L-arginine (mM) | TWEEN-80 (%) | pH |
|---|---|---|---|---|---|
| 5 | 10 | 20 | 138 | 0.1 | 6.5 |
| 6 | 20 | 20 | 138 | 0.1 | 6.5 |

The formulations were prepared and sterilized by filtration through 0.22 μm polyvinylidene difluoride (PVDF) membrane. Each formulation was stored at 37° C. in a 2 mL glass vial until analysis or up to 1 month. The purity of each formulation was determined by SEC-HPLC and its biological activity was determined by the reporter gene assay. As shown in Table 6, the preferred formulation provided a high stability for the GLP-1R antibody fusion protein at a concentration of 20 mg/mL, the change in its purity at 37° C. was similar to that at 10 mg/mL, only with non-significant changes, and at the same time, there was no significant difference as to their biological activity,

TABLE 6

Purities and biological activity of GLP-1R antibody fusion protein formulations at different protein concentrations

| No. | Purity (%) 0 Day | Purity (%) 7 Days | Purity (%) 15 Days | Purity (%) 1 Month |
|---|---|---|---|---|
| 5 | 98.3 | 98.2 | 97.6 | 96.7 |
| 6 | 96.6 | 96.85 | 96.5 | 96.05 |

| No. | Activity (EC50) 0 Day | Activity (EC50) 7 Day | Activity (EC50) 15 Day | Activity (EC50) 1 Month |
|---|---|---|---|---|
| 5 | 0.1 nM | 0.08 nM | 0.09 nM | 0.11 nM |
| 6 | 0.06 nM | 0.07 nM | 0.08 nM | 0.08 nM |

EXAMPLE 4

Stability of the Preferred Formulation Under Vibration

We conducted a study on the stability of the preferred formulation under vibration conditions to investigate whether the formulation could provide stability for the GLP-1R antibody fusion protein in vibratory environments, to assess the effect of sample transportation and daily carrying.

The formulation of GLP-1R antibody fusion protein was prepared according to Table 7:

TABLE 7

GLP-1R antibody fusion protein formulation for stability under vibration

| No. | GLP-1R antibody fusion protein concentration (mg/mL) | Citrate concentration (mM) | L-arginine (mM) | TWEEN-80 (%) | pH |
|---|---|---|---|---|---|
| 7 | 10 | 20 | 138 | 0.1 | 6.5 |

A formulation was prepared and sterilized by filtration through 0.22 polyvinylidene difluoride (PVDF) membrane. The formulation was stored in a 2 mL glass vial at 37° C. and placed on a shaker at a speed of 70 rpm until analysis or up to 15 days. The purity of each formulation was determined by SEC-HPLC, and the biological activity was determined by the reporter gene assay. As shown in Table 8, the stability and biological activity of the GLP-1R antibody fusion protein were maintained under the vibratory conditions.

TABLE 8

Purities and biological activity of GLP-1R Antibody Fusion Protein Formulation under vibration

| No. | Purity (%) 0 Day | Purity (%) 1 Day | Purity (%) 5 Days | Purity (%) 10 Days | Purity (%) 15 Days |
|---|---|---|---|---|---|
| 7 | 98.8 | 99.5 | 99.5 | 99.5 | 99.6 |

| No. | Activity (EC50) 0 Day | Activity (EC50) 1 Day | Activity (EC50) 5 Days | Activity (EC50) 10 Days | Activity (EC50) 15 Days |
|---|---|---|---|---|---|
| 7 | 0.13 nM | 0.13 nM | 0.13 nM | 0.14 nM | 0.16 nM |

EXAMPLE 5

Accelerated Study on Stability of the Preferred Formulation

We performed an accelerated stability study on the preferred formulation to rapidly examine the trend of the changes in the stability of the GLP-1R antibody fusion protein in the preferred formulation over time.

The formulation of the GLP-1R antibody fusion protein was prepared according to Table 9:

TABLE 9

GLP-1R antibody fusion protein formulation for accelerated stability study

| No. | GLP-1R antibody fusion protein concentration (mg/mL) | Citrate concentration (mM) | L-arginine (mM) | TWEEN-80 (%) | pH |
|---|---|---|---|---|---|
| 8 | 10 | 20 | 138 | 0.1 | 6.5 |

The formulation was prepared and sterilized by filtration through 0.22 μm polyvinylidene difluoride (PVDF) membrane. The formulation was stored at 25° C. in a 2 mL glass vial until analysis or up to 6 months. The purity of each formulation was determined by SEC-HPLC and its biological activity was determined by the reporter gene assay. As shown in Table 10, the GLP-1R antibody fusion protein formulation withstood a storage temperature of 25° C. for at least 6 months with no significant changes in the purity and biological activity, showing superior stability.

TABLE 10

Purities and biological activity GLP-1R antibody fusion protein formulation under accelerated conditions

| No. | Purity (%) 0 Month | Purity (%) 0.5 Month | Purity (%) 1 Month | Purity (%) 2 Months | Purity (%) 4 Months | Purity (%) 6 Months |
|---|---|---|---|---|---|---|
| 8 | 98.4% | 98.6% | 98.8% | 99.4% | 97.6% | 96.9% |

| No. | Activity (EC50) 0 Month | Activity (EC50) 0.5 Month | Activity (EC50) 1 Month | Activity (EC50) 2 Months | Activity (EC50) 4 Months | Activity (EC50) 6 Months |
|---|---|---|---|---|---|---|
| 8 | 0.17 nM | N/A | 0.09 nM | 0.08 nM | 0.1 nM | 0.05 nM |

N/A = not tested.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the claims of the present invention.

What is claimed is:

1. A stable pharmaceutical solution formulation of a GLP-1R antibody fusion protein, comprising the GLP-1R antibody fusion protein at a final concentration ranging from 0.1 mg/mL to 100 mg/mL, an amino acid at a final concentration ranging from 1 to 500 mM, a surfactant at a final concentration ranging from 0.01% to 0.5%; and a citrate buffer at a final concentration ranging from 5 to 30 mM, wherein the stable solution formulation has a pH value ranging from 5.0 to 8.0; wherein the GLP-1R antibody fusion protein comprises a light chain variable domain of SEQ ID NO: 1, SEQ ID NO: 2, SEQ ID NO: 3, SEQ ID NO: 4, SEQ ID NO: 5, or SEQ ID NO: 6; and a heavy chain variable domain of SEQ ID NO: 7, SEQ ID NO: 8, or SEQ ID NO: 9; and wherein the amino acid is arginine and the surfactant is a polyoxyethylene sorbitan monolaurate.

2. The stable solution formulation of claim 1, wherein the stable solution formulation is stable for at least 6 months at 25° C.

3. The stable solution formulation of claim 1, wherein the final concentration of the amino acid is 80-200 mM, the final concentration of the surfactant is 0.01%-0.2%, and the pH of the stable solution formulation is from 5.5 to 7.0.

4. The stable solution formulation of claim 1, wherein the final concentration of the citrate buffer is 20 mM.

5. The stable solution formulation of claim 3, wherein the amino acid is L-arginine and the final concentration of L-arginine is 100-180 mM.

6. The stable solution formulation of claim 5, wherein the final concentration of L-arginine is 138 mM.

7. The stable solution formulation of claim 3, wherein the surfactant is TWEEN-80 and the final concentration of TWEEN-80 is 0.05%-0.15%.

8. The stable solution formulation of claim 7, wherein the final concentration of TWEEN-80 is 0.1%.

9. The stable solution formulation of claim 1, wherein the final concentration of the GLP-1R antibody fusion protein is 5 mg/mL-40 mg/mL.

10. The stable solution formulation of claim 1, wherein the GLP-1R antibody fusion protein comprises a light chain variable domain of SEQ ID NO: 3 or SEQ ID NO: 4 ; and a heavy chain variable domain of SEQ ID NO: 8.

11. The stable solution formulation of claim 10, wherein the GLP-1R antibody fusion protein further comprises a light chain constant domain of SEQ ID NO: 10 or SEQ ID NO: 11, and a heavy chain constant domain of SEQ ID NO: 12.

12. The stable solution formulation of claim 1, wherein the final concentration of the GLP-1R antibody fusion protein is 5 mg/mL-40 mg/mL, the final concentration of L-arginine is 138 mM, the final concentration of TWEEN-80 is 0.1%, and the pH is between 6-7.

13. The stable solution formulation of claim 12, wherein the final concentration of the GLP-1R antibody fusion protein is 5 mg/mL.

14. The stable solution formulation of claim 12, wherein the final concentration of the GLP-1R antibody fusion protein is 10 mg/mL.

15. The stable solution formulation of claim 12, wherein the final concentration of the GLP-1R antibody fusion protein is 20 mg/mL.

16. The stable solution formulation of claim 12, wherein the final concentration of the GLP-1R antibody fusion protein is 30 mg/mL.

17. The stable solution formulation of claim 12, wherein the final concentration of the GLP-1R antibody fusion protein is 40 mg/mL.

18. The stable solution formulation of claim 12, wherein the pH is about 6.5.

19. The stable solution formulation of claim 1, wherein the stable solution formulation is stored in a sterile syringe.

20. The stable solution formulation of claim 1, wherein the GLP-1R antibody fusion protein comprises a light chain variable domain of SEQ ID NO: 3 and a heavy chain variable domain of SEQ ID NO: 8.

21. The stable solution formulation of claim 1, wherein the GLP-1R antibody fusion protein comprises a light chain variable domain of SEQ ID NO: 4 and a heavy chain variable domain of SEQ ID NO: 8.

* * * * *